(12) United States Patent
Hunger et al.

(10) Patent No.: US 12,728,214 B2
(45) Date of Patent: Sep. 8, 2026

(54) MEDICAL FLUID PUMP WITH POSSIBILITY OF REMOTE ASSISTANCE

(71) Applicant: W.O.M. World of Medicine GmbH, Berlin (DE)

(72) Inventors: Christian Hunger, Oranienburg (DE); Erika Mase, Berlin (DE); Henrik Stier, Berlin (DE); Jan-Hendrik Carstens, Berlin (DE); Julia Grundmann, Berlin (DE); Hans-Joachim Cappius, Berlin (DE)

(73) Assignee: Novanta Medical GmbH, Berlin (DE)

( * ) Notice: Subject to any disclaimer, the term of this patent is extended or adjusted under 35 U.S.C. 154(b) by 617 days.

(21) Appl. No.: 18/144,674

(22) Filed: May 8, 2023

(65) Prior Publication Data

US 2023/0364359 A1 Nov. 16, 2023

(30) Foreign Application Priority Data

May 6, 2022 (DE) ............................ 102022001604

(51) Int. Cl.
*A61M 13/00* (2006.01)
*G09B 23/28* (2006.01)
(Continued)

(52) U.S. Cl.
CPC ........... *A61M 13/003* (2013.01); *G09B 23/28* (2013.01); *G09B 23/285* (2013.01); *G16H 20/40* (2018.01);
(Continued)

(58) Field of Classification Search
CPC ........ A61M 13/003; A61M 2205/3334; A61M 2205/3344; A61M 2205/3375;
(Continued)

(56) References Cited

U.S. PATENT DOCUMENTS 6,141,584 A 10/2000 Rockwell et al.
2012/0197580 A1 * 8/2012 Vij ..................... A61M 16/024 702/114

(Continued)

FOREIGN PATENT DOCUMENTS

EP 3923297 A1 12/2021
WO WO 2012/040221 A2 3/2012
WO WO 2013/091814 A2 6/2013

OTHER PUBLICATIONS

Examination Report Excerpt of Priority DE 102022001604.4 (no date).

(Continued)

*Primary Examiner* — Tasnim Mehjabin Ahmed
(74) *Attorney, Agent, or Firm* — McCarter & English, LLP; David J. Silvia

(57) ABSTRACT

The present invention relates to operating modes of a medical device for support and device training by a service person connected via data line. In particular, the invention relates to the simulation of operating modes of an insufflator by means of a computer located elsewhere, for example, in a training center. The invention further relates to the simulation of operating conditions of a medical fluid pump by means of a computer located at another location, e.g., in a training center.

20 Claims, 2 Drawing Sheets

(51) Int. Cl.

| | |
|---|---|
| ***G16H 20/40*** | (2018.01) |
| ***G16H 40/40*** | (2018.01) |
| ***G16H 40/63*** | (2018.01) |
| ***G16H 40/67*** | (2018.01) |
| ***G16H 50/50*** | (2018.01) |

(52) U.S. Cl.
CPC ............. *G16H 40/40* (2018.01); *G16H 40/63* (2018.01); *G16H 40/67* (2018.01); *G16H 50/50* (2018.01); *A61M 2205/3334* (2013.01); *A61M 2205/3344* (2013.01); *A61M 2205/3375* (2013.01); *A61M 2205/502* (2013.01); *A61M 2205/581* (2013.01)

(58) Field of Classification Search
CPC ...... G09B 23/28; G09B 23/285; G16H 40/40; G16H 40/63; G16H 40/67
See application file for complete search history.

(56) References Cited

U.S. PATENT DOCUMENTS

| | | | | |
|---|---|---|---|---|
| 2015/0206457 | A1* | 7/2015 | Zamierowski ....... | G09B 23/285 434/268 |
| 2017/0173276 | A1 | 6/2017 | Alkhamesi et al. | |

OTHER PUBLICATIONS

W.O.M World of Medicine, Stryker, Pneumoclear—CO2 Conditioning Insufflator, Sep. 21, 2020, pp. 1-77.
English Translation of PCT International Search Report dated Sep. 28, 2023 for PCT/EP2023/062114.

* cited by examiner 1
2
3
4
5
6
7
8
9
10
11
13
14
15
16
p
V

MEDICAL FLUID PUMP WITH POSSIBILITY OF REMOTE ASSISTANCE

CROSS REFERENCE TO RELATED APPLICATION

This application claims priority to German Patent Application No. 102022001604.4 filed May 6, 2022 entitled Medical Fluid Pump with Possibility of Remote Assistance, the entire contents of which are hereby incorporated by reference.

FIELD OF THE INVENTION

The present invention relates to operating modes of a medical device for support and device training by a service person connected via data line.

STATE OF THE ART

Remote support or remote maintenance has already been described for some time, e.g. in DE2350371C3 "Method and device for testing and maintenance of data processing systems by means of spatially remote maintenance stations". The possibility of connection via existing network connections has also already been described, e.g. in U.S. Pat. No. 6,473,788B1 "Remote maintenance and servicing of a network peripheral device over the world wide web" or EP1450542B1 "Remote maintenance and servicing of a network peripheral device over the world wide web".

Further prior art is formed by the documents WO 2012/040221 A2, WO 2013/091814 A2 as well as US 2017/0173276 A1.

What is not yet known is a solution for training or product training for medical devices via such a network or Internet connection. Here, it must be ensured in particular that no settings harmful to the patient can be made via the remote connection in order to protect the patient. It must also be ensured that no unauthorized external interventions are carried out during ongoing treatment. The risk here is that effects can be detected on site—on the patient or by looking into equipment that is also in use, such as an anesthesia monitor—which cannot be reliably accessed by the remote user. Thus, device control or use via remote connection must be reliably ruled out during patient treatment.

SUMMARY OF THE DISCLOSURE

Disclosed is, inter alia, an insufflator for minimally invasive surgery that includes: a gas connection with proportional valve; a first trocar; a gas supply line for gas from the gas connection with pressure sensor, gas flow sensor and connection to the first trocar; a suction device with adjustable suction power; a second trocar with suction hose, connected to the suction device with adjustable suction power; an electronic control unit; a display device; and an interface to a remote computer. Wherein the electronic control unit transmits current settings of the insufflator to the remote computer via the interface. Additionally, the remote computer simulates treatment of a patient and transmits operating values resulting from the simulation back to the insufflator via the interface; and still further, the display device of the insufflator displays the simulated operating values.

In a preferred embodiment, the insufflator indicates visually and/or acoustically when a simulation is performed.

Preferably, the insufflator completely blocks a gas flow during simulation.

In certain embodiments, the insufflator is connected to a dummy during simulation.

In a preferred embodiment, the remote computer performs the simulation of the treatment by connecting a second identical insufflator, wherein the identical insufflator is connected to a dummy. In certain constructions, the remote computer performs the simulation of the treatment by means of software.

In an embodiment of the present disclosure, the insufflator additionally includes a voice or video connection to the remote computer.

It is presently preferred that in certain embodiments, the remote computer also simulates device, accessory and/or sequence errors as part of the simulation.

Figure 1:
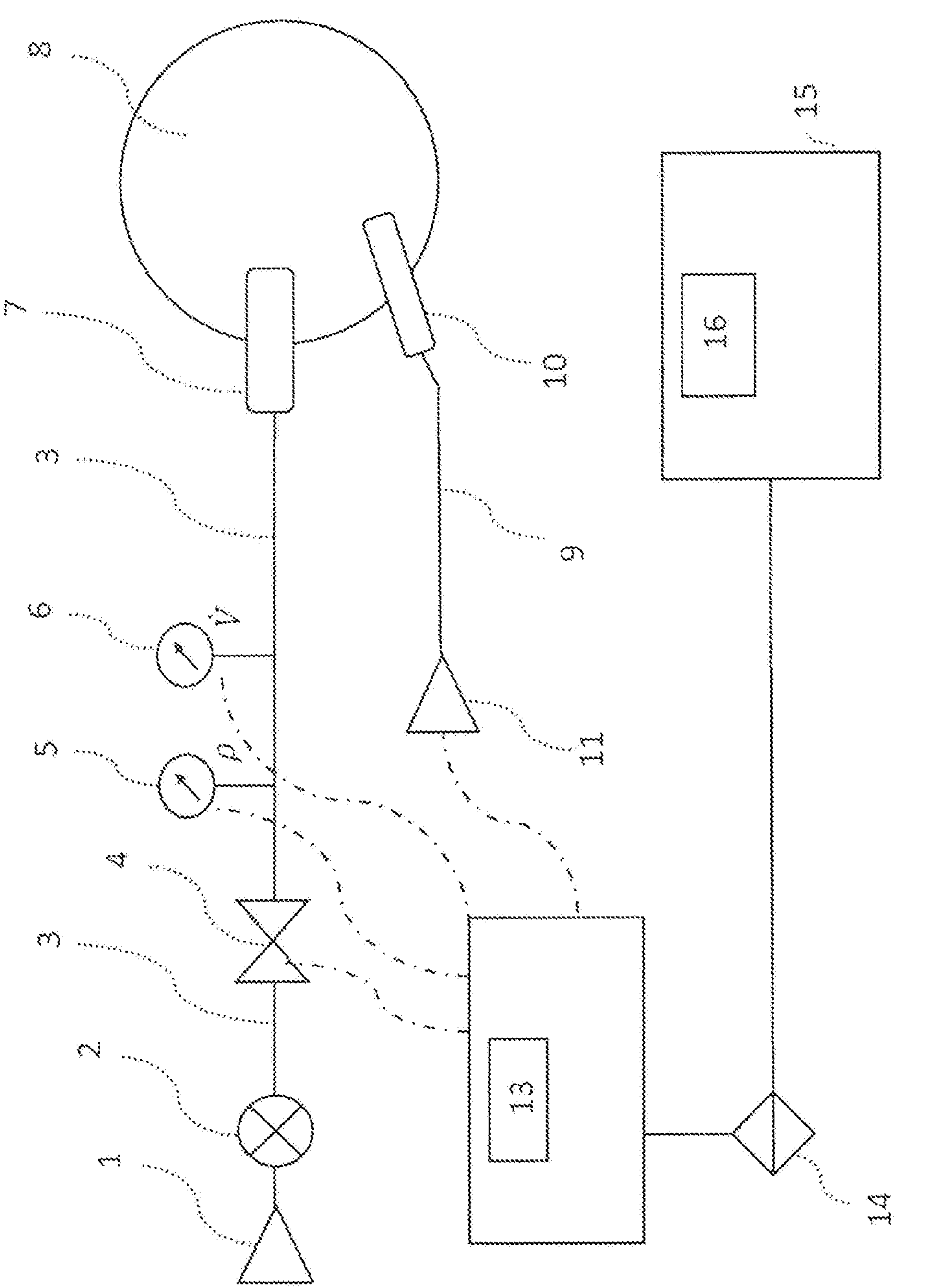
FIG. 1 illustrates an embodiment of the present invention.
Figure 2:
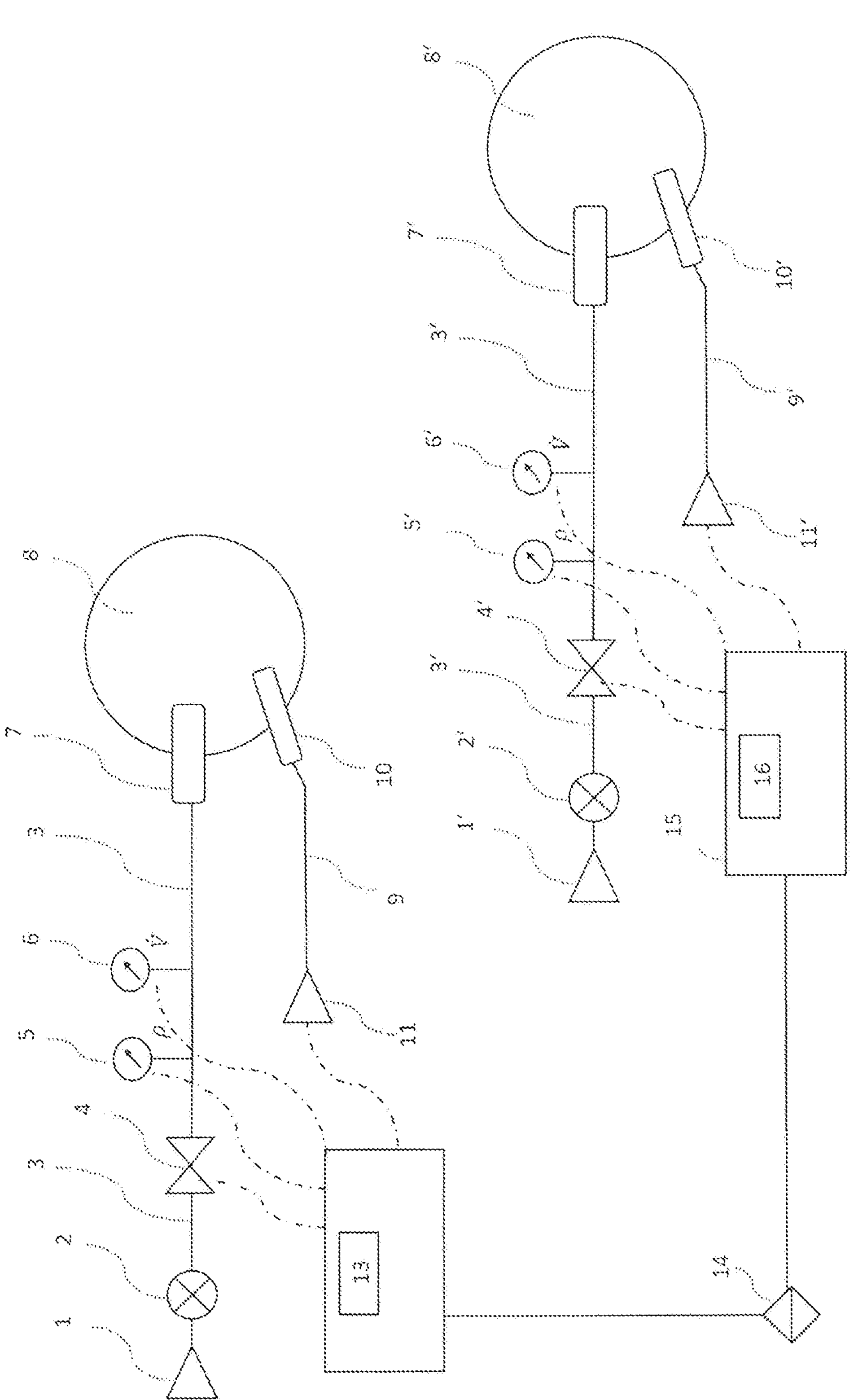
FIG. 2 shows an embodiment in which an insufflator according to the invention is connected to a second insufflator of identical design.

The reference numbers used in FIG. 1 have the following meanings:

- (1) gas connection
- (2) proportional valve
- (3) Gas supply line
- (4) Volume flow control
- (5) pressure sensor
- (6) volume flow sensor
- (7) first trocar
- (8) cavity
- (9) suction hose
- (10) second trocar
- (11) suction unit with adjustable suction power (optional)
- (12) electronic control unit
- (13) display unit
- (14) interface
- (15) remote computer
- (16) display device of the remote computer The reference numbers used in FIG. 2 have the following meaning:

- (1)/(1') gas connection
- (2)/(2') Proportional valve
- (3)/(3') Gas supply line
- (4)/(4') Volume flow control
- (5)/(5') Pressure sensor
- (6)/(6') Volume flow sensor
- (7)/(7') First trocar
- (8)/(8') cavity
- (9)/(9') suction hose
- (10)/(10') second trocar
- (11)/(11') suction device with adjustable suction power (optional)
- (12)/(12') electronic control unit
- (13)/(13') display unit
- (14) interface
- (15) remote computer
- (16) display device of the remote computer

DETAILED DESCRIPTION OF PREFERRED EMBODIMENTS

The invention relates in a first aspect to an insufflator for minimally invasive surgery which is adapted to allow support, in particular simulation, of operating conditions from a distance.

With reference to FIG. 1, in a first embodiment, the invention relates to an insufflator for minimally invasive surgery that includes: a gas connection with proportional valve; a first trocar; a gas supply line for gas from the gas connection with pressure sensor, gas flow sensor and connection to the first trocar; a suction device with adjustable suction power; a second trocar with suction hose, connected to the suction device with controllable suction power; an electronic control unit; a display device; and an interface to a remote computer.

The electronic control unit transmits the current settings of the insufflator to the remote computer via the interface. Additionally, the remote computer simulates the treatment of a patient and transmits the operating values resulting from the simulation back to the insufflator via the interface and the display unit of the insufflator displays simulated operating values.

An insufflator is basically a medical device as described in manifold embodiments in the prior art. A detailed explanation of the individual components and functions of an insufflator is therefore unnecessary here.

In an embodiment of such an insufflator according to the invention, the insufflator includes an interface to a computer which is located remotely, i.e. at a different location. The distance of the insufflator from the remote computer may therefore be practically arbitrary. It is therefore possible to interface the insufflator located in a clinic with a computer located, for example, in a training center of the insufflator manufacturer. Corresponding transmission protocols are known in principle, also for secure transmissions. The remote computer simulates a treatment, as shown below, and transmits the operating values resulting from the simulation back to the insufflator. In this way, personnel can become familiar with the operation of the insufflator.

To ensure patient safety, the insufflator typically displays that the device is running in a simulation mode. The display can be visual and/or audible.

During the simulation, it is expedient to ensure that the gas flow of the insufflator is completely blocked so that the simulation of unusual operating conditions is not inadvertently performed on an actual patient.

However, in specific embodiments of the invention, it is also possible to connect the insufflator to a dummy to try out additional functions. By a dummy is meant an artificial test object that has similar properties to a body part connected to the medical device. This can be, for example, an elastic balloon that can be expanded like an abdomen. It can of course also be a manikin (possibly equipped with sensors) whose size and weight ratios correspond to those of a human being, with corresponding cavities that allow expansion by means of gas or liquid. An operating mode with the aid of a dummy also permits, for example, the changing of hoses, for example in the simulation of hose occlusions, but also the procedures in the event of possible leaks.

In such an operating mode, however, it must be ensured that a dummy and not a patient is actually connected before a gas flow is actually generated. This can be done, for example, by providing hoses and dummy for the simulation mode with special data carriers. These may be, for example, RFID modules that signal to the insufflator that special simulation hoses and a dummy are connected.

Another embodiment of the invention is that the remote computer is connected to a second identical insufflator. FIG. 2 represents such an embodiment. This identical insufflator may be connected to a dummy, for example. In this embodiment, it is possible to perform the simulation using the second identical insufflator and to transmit the operating values measured in the simulation setup (for example, pressures, volume flows, etc.) back to the first simulator.

As an alternative to the embodiment with a second identical insufflator, it is of course also possible to run the simulation on software. This software is usually run on the second computer so that the operating conditions can be simulated remotely, for example controlled by training personnel in the insufflator manufacturer's training center. In this way, the training personnel can teach the operation of the insufflator, including the correction of errors or the handling of unusual operating conditions (for example, caused by a tube occlusion).

It makes sense to have a voice or video connection between the training personnel and the insufflator operator (e.g. doctor) during the simulation in addition to the data connection. For this purpose, a video conferencing tool can be used, which can also be integrated into the insufflator. In this way, the training personnel have the opportunity to identify operating errors and communicate corrections.

In a further alternative embodiment of the invention, the software for simulating operating conditions can also be run directly on the insufflator. In this case, too, it must be ensured that no patient is connected to the insufflator during the simulation. Analogous to the possibilities described above, in this case the gas flow can also either be completely blocked or safety measures can be taken to ensure that only a dummy is connected to the insufflator. In this case, the simulated operating conditions are transmitted to the remote computer (e.g. in the training center) so that the training personnel can monitor the simulation. In this case, too, a voice or video connection with the training personnel is recommended for monitoring the simulation and correcting any errors that may occur.

The present disclosure also relates to an insufflator for minimally invasive surgery that includes: a gas connection with proportional valve; a first trocar; a gas supply line for gas from the gas connection with pressure sensor, gas flow sensor and connection to the first trocar; a suction device with adjustable suction power; a second trocar with suction hose, connected to the suction device with adjustable suction power; an electronic control unit; a display device; and an interface to a remote computer, The electronic control unit runs software which simulates the treatment of a patient on the basis of the current settings of the insufflator and displays the operating values resulting from the simulation on the display unit of the insufflator and on the remote computer.

Therefore, the solution according to the invention consists in a special operating mode that does not allow the pumping or draining of expansion medium into a patient.

All the steps triggered on the device by the user are represented in the preferred operating mode purely by display on the input/operator interface of the medical device, without controlling the corresponding actuators in the device. The device is thus used for pure simulator operation. In this case, this user interface is preferably superimposed with a clearly recognizable visual signal, e.g. a watermark "training mode" or a special coloring of the user interface. Alternatively or in parallel, the training state can be indicated by an acoustic signal, e.g. a phrase "Training mode-press "Exit" to return to patient treatment" played repeatedly when a key is pressed. This signaling serves to prevent a user from assuming that a patient treatment can be performed in the current mode.

For the solution according to the invention, a network connection is required as a prerequisite on the device. This can be designed as an internet access or other connection to a network, where in the network a remotely located technician or expert has a data connection to the device. Optionally, this technician has a parallel voice/video connection to a user to be trained or supported at the medical device.

In the "remote training" embodiment, the user's input is taken over and translated into calculated display values either by a sequence control stored in the device or via a remote connection with sequence control by a remote computer. These display values are accompanied by explanations of the changes taking place—in text form, as an audio recording or by a remote technician or expert. The timed sequences include not only the expected and achievable behavior, but also disturbances and unexpected display values to train the user in trouble shooting, troubleshooting and counter reactions in case of undesired conditions. According to the invention, the listening/talking connection to the technician can be established by the medical device. Also according to the invention, it is possible to establish a listening/talking connection or video conference with the instructor in parallel. In both cases (audio/speech connection through the medical device or through a parallel possibility), the teacher has remote access to the user interface of the medical device, i.e., he/she can both see the display that the user is observing himself/herself and influence its values, make an interaction or start training sessions that process certain display values and user inputs. According to the invention, when the remotely seated instructor interacts, his interaction is visually indicated, e.g., with a mouse cursor or finger icon, which points to the element being operated.

The invention also includes a computer program which runs on the remote computer and simulates the execution of a medical procedure, i.e. accepts the user input and, over time, according to the given situation, either generates messages on the medical device which do not correspond to the usual procedure but to the imparting of user knowledge, or simulates the usual behavior of the medical device with the possibility of generating error cases or critical states and training the user's solution options. For example, a message could be "Tube set occlusion!", whereupon a selection of possible actions are displayed to the user as possible choices. This can be done on the touchscreen of the medical device or via the designation of the selection options on the control elements, e.g. keys with microswitches, if these are placed at the edge of the screen, for example.

The knowledge imparted via these computer programs covers everything that is necessary during product training:

- Commissioning of the medical device,
- Meaning of the displays,
- setting options and their storage,
- stored selection options or presettings,
- sequences in a medical procedure—in each case for the procedures typically performed with the medical device,
- possible error messages, alarms and warnings and their meaning,
- Correction of conditions that lead to error messages or insufficient performance of the medical device,
- demonstration of visual and acoustic signaling, acknowledgement of signaling,
- etc.

Likewise, a "support" mode of operation according to the invention allows a user in a critical situation to call in an external expert who can assess the observed and explained situation, see all device parameters including the user interface, but cannot make any adjustments. This "support" mode is restricted in such a way to exclude patient treatment, i.e. to allow only one direction of information transport (medical device to external) when requested during a medical procedure with patient treatment.

In furtherance of the present invention, for device control, a message may be acknowledged or an assigned control pressed by an externally connected device on the medical device to authorize execution.

In an even more advanced "service" mode of operation, a connection can be made at the medical device to a service center to allow new operating software/updates to be applied there or to allow data on the status of the medical device to be read out via a connection from the medical device to a device in the service center.

According to the invention, such a connection requires various security aspects, such as, among others:

- Reading the serial number, or unique identifier, of the medical device,
- End-to-end encryption of all data sent and received,
- sending instructions to specific hardware elements and evaluating the response generated in execution, such as components with generation of specific codes in response to a request (e.g., so-called crypto-chips).
- execution of an update of the operating software only after interaction on site (e.g. keystroke by the user), in order to exclude an accidental update during a procedure.

Other prior art security elements are also considered to be in accordance with the invention.

The invention is equally practicable in other forms, such as joint arthroscopy, in which adapted irrigation pumps (e.g., roller wheel pumps) are used to pump fluid into a joint for the purpose of distension.

The invention also relates to a medical fluid pump for minimally invasive surgery, that includes: a fluid reservoir, a first trocar; a fluid supply line for fluid from the reservoir with pressure sensor, flow sensor and connection to the first trocar; a liquid suction device with adjustable suction power; a second trocar with suction hose, connected to the liquid suction device with adjustable suction power; an electronic control unit; a display unit; and an interface to a remote computer, The electronic control unit communicates the current settings of the medical fluid pump to the remote computer via the interface. Additionally, the remote computer simulates the treatment of a patient and transmits the operating values resulting from the simulation back to the medical fluid pump via the interface-, wherein the display unit of the medical fluid pump displays the simulated operating values.

The medical fluid pump is basically a medical device as described in various forms in the state of the art. A detailed explanation of the individual components and functions is therefore unnecessary here.

The functions and modes of operation of such a medical fluid pump according to the invention correspond to those of the insufflators described above, so that reference can be made thereto in order to avoid repetition.

The invention also relates in an analogous manner to a medical fluid pump for minimally invasive surgery that includes: a fluid reservoir; a first trocar; a fluid supply line for fluid from the reservoir with pressure sensor, flow sensor and connection to the first trocar; a liquid suction device with adjustable suction power; a second trocar with suction hose, connected to the liquid suction device with adjustable suction power; an electronic control unit; a display unit; and an interface to a remote computer, in which the electronic control unit runs software which simulates the treatment of a patient on the basis of the current settings of the medical fluid pump and displays the operating values resulting from the simulation on the display unit of the medical fluid pump and on the remote computer.

What is claimed is:

1. An insufflator for minimally invasive surgery, comprising:
a) a gas connection with proportional valve;
b) a first trocar;
c) a gas supply line for gas from the gas connection with pressure sensor, gas flow sensor and connection to the first trocar;
d) a suction device with adjustable suction power;
e) a second trocar with suction hose, connected to the suction device with adjustable suction power;
f) an electronic control unit;
g) a display device; and
h) an interface to a remote computer,
wherein the electronic control unit transmits current settings of the insufflator to the remote computer via the interface;
wherein the remote computer simulates treatment of a patient and transmits operating values resulting from the simulation back to the insufflator via the interface;
wherein the remote computer performs the simulation of the treatment by connecting a second identical insufflator,
wherein the identical insufflator is connected to a dummy; and
wherein the display device of the insufflator displays the simulated operating values.

2. The insufflator according to claim 1, wherein the insufflator indicates visually and/or acoustically when a simulation is performed.

3. The insufflator according to claim 1, wherein the insufflator completely blocks a gas flow during simulation.

4. The insufflator according to claim 1, wherein the insufflator is connected to a dummy during simulation.

5. The insufflator according to claim 1, wherein the remote compute performs the simulation of the treatment by means of software.

6. The insufflator according to claim 1, wherein the insufflator additionally comprises a voice or video connection to the remote computer.

7. The insufflator according to claim 1, wherein the remote computer also simulates device, accessory and/or sequence errors as part of the simulation.

8. An insufflator for minimally invasive surgery, comprising
a) a gas connection with proportional valve;
b) a first trocar;
c) a gas supply line for gas from the gas connection with pressure sensor, gas flow sensor and connection to the first trocar;
d) a suction device with adjustable suction power;
e) a second trocar with suction hose, connected to the suction device with adjustable suction power;
f) an electronic control unit;
g) a display device; and
h) an interface to a remote computer,
wherein the electronic control unit runs software which simulates treatment of a patient on the basis of current settings of the insufflator and displays operating values resulting from the simulation on the display device of the insufflator and on the remote computer;
wherein the remote computer performs the simulation of the treatment by connecting a second identical insufflator, and
wherein the identical insufflator is connected to a dummy.

9. The insufflator according to claim 8, wherein the insufflator visually and/or acoustically indicates when a simulation is being performed.

10. The insufflator according to claim 8, wherein the insufflator completely blocks a gas flow during the simulation.

11. The insufflator according to claim 8, wherein the insufflator is connected to a dummy during simulation.

12. The insufflator according to claim 8, wherein the remote computer also simulates device, accessory and/or sequence failures during the simulation.

13. A medical device fluid pump for minimally invasive surgery, comprising:
a) a fluid reservoir;
b) a first trocar;
c) a fluid supply line for fluid from the reservoir with pressure sensor, flow sensor and connection to the first trocar;
d) a liquid suction device with adjustable suction power;
e) a second trocar with suction hose, connected to the liquid suction device with adjustable suction power;
f) an electronic control unit;
g) a display unit; and
h) an interface to a remote computer,
wherein the electronic control unit communicates current settings of the medical device fluid pump to the remote computer via the interface;
wherein the remote computer simulates treatment of a patient and transmits operating values resulting from the simulation back to the medical fluid pump via the interface;
wherein the remote computer performs the simulation of the treatment by connecting a second identical insufflator;
wherein the identical insufflator is connected to a dummy; and
wherein the display unit of the medical device fluid pump displays the simulated operating values.

14. The medical device fluid pump according to claim 13, wherein the medical device fluid pump additionally comprises a voice or video connection to the remote computer.

15. The medical device fluid pump according to claim 13, wherein the remote computer also simulates device, accessory, and/or procedure errors as part of the simulation.

16. A medical fluid pump for minimally invasive surgery, comprising:
a) a fluid reservoir;
b) a first trocar;
c) a fluid supply line for fluid from the reservoir with pressure sensor, flow sensor and connection to the first trocar;
d) a liquid suction device with adjustable suction power;
e) a second trocar with suction hose, connected to the liquid suction device with adjustable suction power;
f) an electronic control unit;
g) a display unit; and
h) an interface to a remote computer,
wherein the electronic control unit runs software which simulates treatment of a patient based on the current settings of the medical fluid pump and displays the operating values resulting from the simulation on the display unit of the medical fluid pump and on the remote computer:

wherein the remote computer performs the simulation of the treatment by connecting a second identical medical fluid pump, and wherein the identical medical fluid pump is connected to a dummy.

17. The medical fluid pump according to claim 16, wherein the medical fluid pump visually and/or audibly indicates when a simulation is being performed.

18. The medical fluid pump according to claim 16, wherein the medical fluid pump completely blocks gas flow during simulation.

19. The medical fluid pump according to claim 16, wherein the medical fluid pump is connected to a dummy during the simulation.

20. The medical fluid pump according to claim 16, wherein the remote computer performs the simulation of the treatment by means of software.

* * * * *